United States Patent [19]

Berry et al.

[11] 4,068,292
[45] Jan. 10, 1978

[54] ELECTROSTATIC SHIELD FOR DIATHERMY TREATMENT HEAD

[75] Inventors: Fred M. Berry, Leawood; James N. Shirley, Kansas City, both of Kans.

[73] Assignee: International Medical Electronics, Inc., Kansas City, Kans.

[21] Appl. No.: 707,529

[22] Filed: July 22, 1976

Related U.S. Application Data

[63] Continuation-in-part of Ser. No. 562,568, March 27, 1975, abandoned.

[51] Int. Cl.² .............................................. A61N 1/06
[52] U.S. Cl. ................................... 361/437; 128/404; 219/6.5; 361/212
[58] Field of Search .............. 219/6.5, 10.5 SF, 10.81, 219/10.57, 10.41, 10.43; 128/404, 411, 418, 421, 422; 361/212, 437

[56] References Cited

U.S. PATENT DOCUMENTS

| | | | |
|---|---|---|---|
| 1,909,982 | 5/1933 | Parker | 219/6.5 X |
| 2,047,159 | 7/1936 | Wood et al. | 174/35 CE |
| 3,368,565 | 2/1968 | Kendall et al. | 128/404 |
| 3,898,410 | 8/1975 | Peters | 361/212 |

Primary Examiner—Harry E. Moose, Jr.
Attorney, Agent, or Firm—Lowe, Kokjer, Kircher, Wharton & Bowman

[57] ABSTRACT

Method and apparatus for minimizing or preventing the deleterious skin heating effects associated with conventional short wave diathermy treatment. The disclosed method includes attenuation of the electrostatic field transmitted by the applicator head and transcutaneous transmission of the radiated electromagnetic energy substantially unimpeded to the deep body tissues to be treated. The attenuation of the electrostatic field is performed by an electrostatic shield, which is adapted to be positioned on the diathermy applicator head between the radiating electrode and the patient receiving treatment. However, the radiated electromagnetic field, which is primarily responsible for the therapeutic generation of heat in relatively deep body tissues, passes through the shield substantially unimpeded. The shield comprises a plurality of narrow, preferably metallic, spaced apart strips and an electrically conductive loop which surrounds the strips and is coplanar therewith. Each of the strips are oriented generally perpendicular with respect to both the current carrying coils in the applicator head (on which the shield is mounted) and the loop. The strips extend generally radially outwardly from the loop center area toward the loop, to which each of the strips is electrically connected. So positioned, the strips impede electrostatic field radiation while facilitating passage of the electromagnetic field. The loop further reduces electrostatic field radiation by discouraging fringing effects, but its radius is sufficiently large to prevent interference with the radiated magnetic field.

20 Claims, 4 Drawing Figures

ELECTROSTATIC SHIELD FOR DIATHERMY TREATMENT HEAD

BACKGROUND AND SUMMARY OF THE INVENTION

This application is a continuation-in-part of pending application Ser. No. 562,568, filed Mar. 27, 1975 now abandoned. In particular, this invention relates to apparatus for reducing the electrostatic field radiated by conventional diathermy apparatus in the heat treatment of internal body tissues without significant skin surface heating effects.

Medical diathermy involves the use of high frequency electric currents for the therapeutic heat treatment of body tissues. The radio frequencies employed are sufficiently high so that nerves and muscles are not adversely stimulated. The applied intensity is sufficiently low so that the temperature developed in the tissue is below that required to destroy the tissue or impair its vitality.

Radio frequency currents generated by the diathermy machine are controllably applied to the patient via the diathermy applicator head, which is designed to transcutaneously transmit high frequency energy to deep afflicted tissue areas. However, the radiated energy must penetrate a layer of skin and fat before reaching the targeted muscle tissue. The fat layer has little vasculation and cooling capacity, and in addition it has a lower specific heat than lower tissues, resulting in a greater temperature rise per unit heat input. Thus, with typical applicator heads, painful heating of the subcutaneous fat layer is not altogether uncommon. Irritating and painful skin burns are also regular incidences of conventional diathermy treatment. In response to initial heating of the skin, perspiration occurs. Perspiration contains a relatively large amount of sodium chloride in solution, and thus perspiration is highly conductive electrically. Steam burns occur when circulating currents in the salt water raise the temperature to the vaporization point.

It has been found that the deleterious surface heating effects just described are primarily caused by the electrostatic fields radiated by conventional diathermy applicators. The matter is discussed, for example, in an article entitled "Therapeutic Application of Electromagnetic Power", which appears at page 55 of Proceedings of the I.E.E.E., Vol. 62, No. 1, Jan., 1974.

The radiated electromagnetic field, however does not cause harmful burning of surface tissues. Instead, it penetrates deeply enough to provide relative heating in the muscle tissues. This deep heating effect results from the fact that the electromagnetic field lines are tangential to the tissue interfaces rather than perpendicular, so that boundary conditions do not significantly affect or cause surface heating effects. Thus the therapeutic deep heating benefits of diathermy treatment are primarily caused by electromagnetic energy. This conclusion refutes learning in the prior art as discussed, for example, at page 285 of a book entitled *Second Edition of Therapeutic Heat and Cold*, edited by Sydney Licht, M.D., published by Waverly Press Inc., Baltimore, Md, 1965.

The instant invention comprises a shield for diathermy heads which greatly attenuates radiated electrostatic fields while permitting the transmission of electromagnetic energy therethrough, and a method for heat treating internal tissues with a diathermy apparatus. The shield comprises a plurality of non-magnetic metallic (preferably copper) strips which are located interiorly of a coplanar, generally circular loop. Each of the strips is orientated generally perpendicular with respect to the current carrying coils in the diathermy applicator head on which the shield is mounted. The width of the strips is quite narrow with respect to the wavelength of the energy radiated by the diathermy applicator head. Each of the strips which extends generally radially outwardly from the vicinity of the loop center, terminating at the loop and being electrically connected thereto. The loop, which is sufficiently large to prevent interference with the electromagnetic field radiated therethrough, provides further electrostatic shielding effects by preventing fringing of the electrostatic field.

In an alternative embodiment of this invention, two preferably circular shields, constructed generally as mentioned above, are stacked together. One of the circular shields may be mounted for relative rotation with respect to the other, so that it can be rotated as desired to control the amount of electrostatic energy passing through to the patient. In a first position the strips in each circular shield are aligned to permit some electrostatic energy to be transmitted to the patient. In a closed position, however, the strips of the first circular shield are aligned between the strips of the second so that transmission (to the patient) of electrostatic field energy is substantially reduced.

The method disclosed by the instant invention comprises the steps of generating radio frequency electric currents to thereby produce electrostatic and electromagnetic energy that can be directed to the body tissue to be treated via the diathermy applicator head. The method also includes the step of attenuating at least a portion of the radiated electrostatic energy before it reaches the exterior skin surface in order to minimize the skin heating effects associated with the diathermy treatment. Finally, the method calls for the transcutaneous transmission of the radiated electromagnetic energy substantially unimpeded to the body tissues to be treated. The attenuation of the electrostatic energy can be best accomplished by using an electrostatic shield mounted on the diathermy applicator head.

It is therefore a fundamental object of the method and apparatus of this invention to reduce the surface heating effects (such as skin burning) associated with conventional shortwave diathermy applicator heads while at the same time facilitating therapeutic muscle treatment. Accordingly, the present invention attenuates the transmission of deleterious electrostatic energy to the patient receiving treatment while permitting the passage of the more desirable electromagnetic energy substantially unimpeded.

Another object of this invention is to provide a shield of the character described which minimizes electromagnetic energy losses. It is a feature of this invention that the width of the conductive strips mentioned above is extremely narrow when compared to the wavelength of the emitted energy. The shorted turn effect is reduced by leaving a space at the center of the loop into which the strips do not extend. Finally, a loop surrounds the strips to prevent electrostatic fringing. Together these features promote the overall efficiency of the shield, facilitating the transmission of electromagnetic energy and impeding the passage of electrostatic energy.

Yet another object of this invention is to provide an electrostatic shield of the character described which can easily be used with a wide variety of diathermy applicator heads. It is a feature of this invention that the aforementioned strips and loop can be attached to the existing applicator heads by glue or adhesive. Also, the strips and loop can be constructed by appropriate metal depositing techniques. For example, the pattern can be metalized on the plastic cover of conventional applicator heads.

Still another object of this invention is to provide means for reducing the detuning effect experienced by diathermy applicator heads when the heads are applied to the desired "load" (which comprises the patient's body). It is a feature of this invention that undesirable electrostatic (capacitive) coupling between the patient's body and the applicator head is significantly reduced when the shield is installed. Thus, when an applicator head incorporating the instant invention is positioned adjacent the patient's body, it will not be severely detuned from resonance. The latter characteristic is a significant synergistic effect exhibited by the instant invention. Thus, when the shield is installed on conventional diathermy heads, operating ease and efficiency are increased and undesirable side effects are reduced.

Another object of this invention is to provide a uniquely constructed "variable" shield for diathermy applicator heads which may be adjusted by the patient (or the operator of the diathermy apparatus) to control a preselected amount of electrostatic energy passing therethrough.

Other and further objects of this invention will become apparent in the course of the following description.

DESCRIPTION OF THE DRAWINGS

In the accompanying drawings, which form a part of the specification and are to be read in conjunction therewith, and in which like reference numerals are employed to indicate like parts in the various views:

Referring now to FIGS. 1 and 2, an electrostatic shield, which is generally indicated by the reference numeral 10, comprises a circumferential loop 11 and a plurality of electrically conductive strips 12. Loop 11 and strips 12 are disposed on a non-metallic mounting surface 13, preferably being affixed to the inner surface thereof by adhesive or the like. Alternatively, the loop and the strips may be metalized on the surface 13 by conventional etching techniques. A plurality of mounting holes 14 are disposed at opposite corners of the shield 10 within loop 11. Shield 10 is secured to the applicator head 15 by mounting screws 16 which extend through holes 14 and are threadedly received within appropriate apertures defined in head 15. Screws 16 affect the proper grounding of loop 11 (and thus shield 10) to the metallic frame or chassis of the applicator head.

Figure 2:
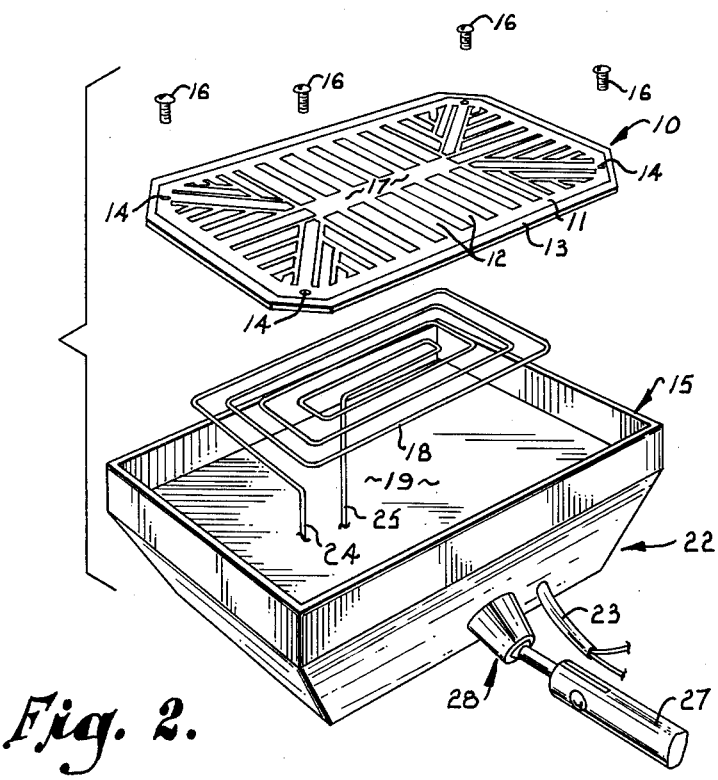
FIG. 2 is an exploded, perspective view of a diathermy applicator head on which the electrostatic shield has been mounted.

Loop 11 must be sufficiently large to avoid interfering with the electromagnetic field radiated by the diathermy applicator head. However, the loop must be close enough to the edges of the applicator head to prevent fringing of the radiated electrostatic fields. Consequently, loop 11 should approximate the size of the applicator head —i.e., just large enough to surround or enclose the underlying current carrying coil 18 within the head (FIG. 2). When the loop is appropriately grounded by screws 16, it will prevent fringing of the electrostatic field radiated by conventional diathermy applicator heads to help prevent surface tissue heating.

Each of the strips 12 (also preferably constructed of copper) extends generally radially outwardly from the center of the area 17 enclosed by loop 11. The strips 12 are coplanar with the loop and are electrically connected thereto by soldering or the like. It is significant to note that the width of the strips 12 is very small in proportion to the wavelength (usually approximately 11 meters) of the energy emitted by the associated diathermy equipment to minimize circulating currents and electromagnetic energy losses associated therewith.

Each strip 12 is oriented substantially perpendicular to loop 11 and to the underlying coil 18 (FIG. 2) in the applicator head. The strips function collectively as a Faraday or an electrostatic shield, effectively isolating the electrostatic field energy emitted by the diathermy head from the patient. Electrostatic field energy will be substantially dissipated in the form of eddy currents in each of the strips 12.

The strips 12 are selectively sized to create the area 17 to avoid the "shorted turn" effect. If, for example, the strips extended across this area, induced currents in the strips from the electromagnetic field would result, thereby subtracting from heating efficiency. The "shorted turn" around the outer edge of the shield (loop 11) is outside of the magnetic field so that electromagnetic energy losses caused by it are minimized.

In FIG. 2, a diathermy applicator head 20 comprises an inductive, spirally wound coil 18 which is housed within a preferably metallic, box-like, generally tapered enclosure 22. Coil 18 is preferably disposed on planar mounting surface 19, which is spaced a predetermined distance from the lower metallic surface of enclosure 22. The said spacing minimizes the effects of the metallic enclosure on the radiated magnetic field. The applicator head is supported by arm 27 which is mechanically linked to the diathermy generator apparatus (not shown). Arm 27 is adjustably attached to enclosure 22 via a conventional ball and socket combination 28. A cable 23, which extends from the generator apparatus, enters the applicator head and delivers RF energy to coil 18 via end portions 24 and 25. Head 15 may be constructed, for example, in accordance with the teachings of an application for Letters Patent owned by the same assignee and entitled "Inductive Applicator Head for Shortwave Diathermy", filed Mar. 3, 1974, assigned Ser. No. 449,372, and which is now abandoned. Surface 13, which is adapted to fit on enclosure 22, comprises the top of the applicator head. For illustration purposes, shield 10 is shown in a functional operating position on the top of mounting surface 13.

Each of the strips 12 is oriented substantially perpendicular to the underlying loops of coil 18, which is substantially surrounded by loop 11. While loop 11 may be grounded in a variety of ways, in the preferred embodiment it is grounded by mounting screws 16 as the surface 13 is reattached to enclosure 22, thereby electrically connecting loop 11 to the chassis of the diathermy applicator head.

When RF energy is applied to coil 18 (via lines 23 and 24) the electrostatic field normally radiated by the applicator head is substantially reduced by the shield 10, thereby minimizing the undesirable surface tissue heating experienced by the patient. At the same time, however, electromagnetic energy passes through shield 10 and enters the patient to provide the desired therapeutic heating effects.

Figure 1:
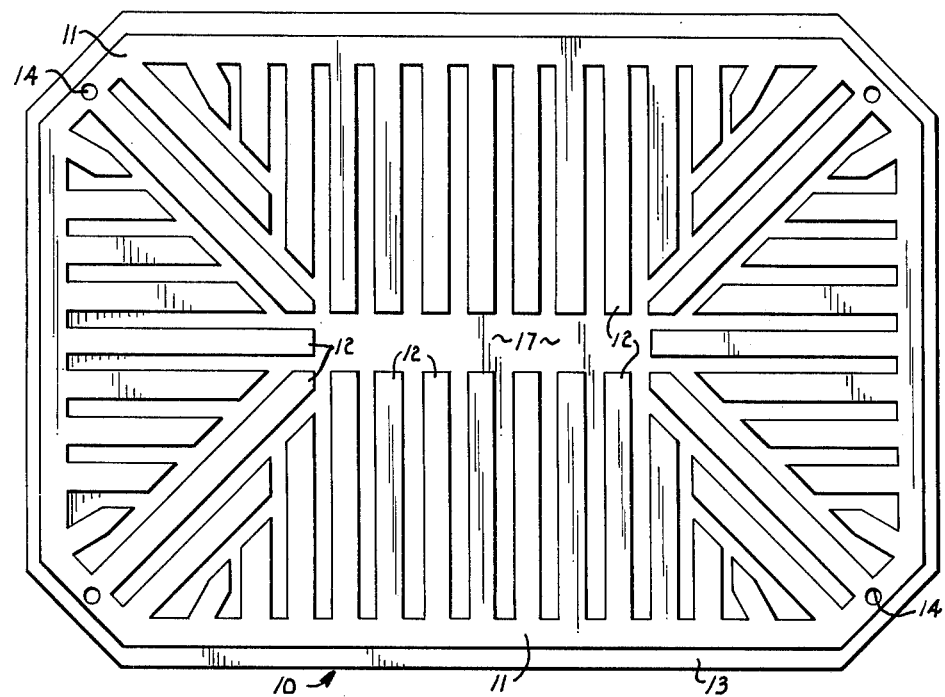
FIG. 1 is a top plan view of an electrostatic shield for diathermy applicator heads constructed in accordance with the teachings of this invention.
Figure 3:
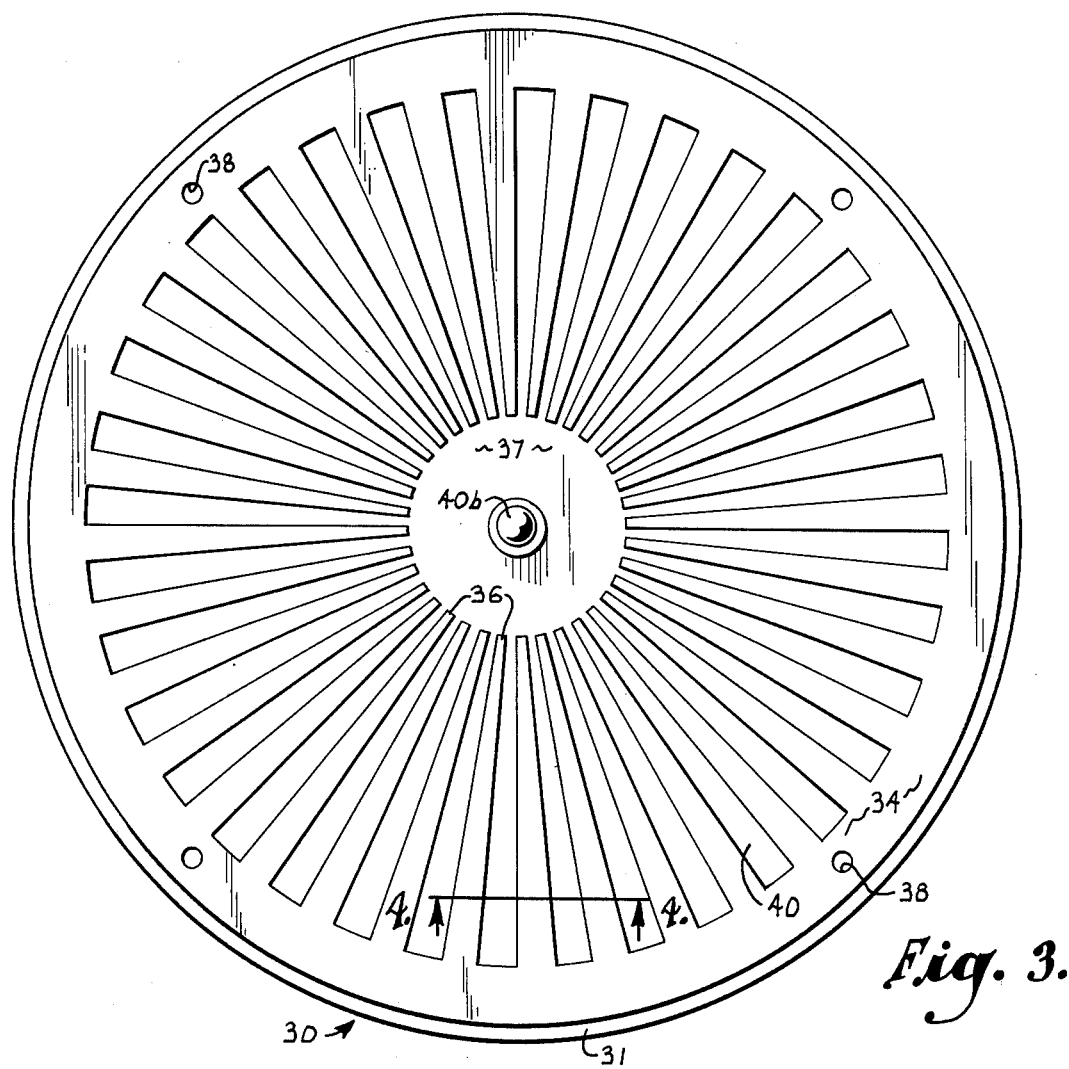
FIG. 3 is a top plan view of an adjustable electrostatic shield for diathermy applicator heads constructed in accordance with the teachings of this invention.
Figure 4:
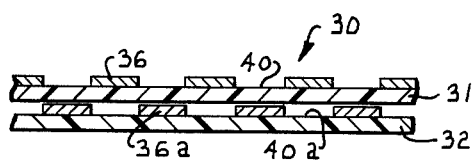
FIG. 4 is a sectional view of the shield taken along line 4—4 of FIG. 3.

In an alternative embodiment of this invention shown in FIGS. 3 and 4, a circular, adjustable shield 30 comprises a pair of stacked shield surfaces 31 and 32. As before, shield 30 is adapted to be positioned between the patient and the current carrying coils in the diathermy applicator head. Each shield surface comprises a circular, electrically conductive loop 34 and a plurality of uniformly spaced apart, electrically conductive strips 36 (or 36a) which extend radially outwardly from a central area 37 toward loop 34. Area 37, which corresponds to area 17 of FIGS. 1 and 2, is electrically non-conductive and thereby avoids the "shorted turn" effect Strips 36 are electrically connected to loop 34. Loop 34 has a plurality of mounting holes 38 defined therein for grounding and mounting it to the frame of an appropriate diathermy applicator head. As discussed previously, the loop will thus prevent electrostatic fringing while the strips will attenuate electrostatic energy passing through the shield.

As seen in FIG. 3, the width of each of the strips 36 increases uniformly between center area 37 and loop 34. Importantly, the dimensions of each space 40 between adjacent strips are substantially identical to the dimensions of the strips 36. Thus, when surface 30 is alignably placed on top of surface 32 and frictionally but rotatably fastened thereto by rivet 40b, it may be rotated to a "closed" position such that strips 36 in surface 31 block underlying spaces 40a in surface 32, and strips 36a in surface 32 block spaces 40 in surface 31. On the other hand, surface 31 may be rotated to an "open" position such that strips 36 directly overlie strips 36a. Obviously a variety of intermediate positions may be selected. Thus shield 30 may be adjusted by the patient (or machine operator) to vary the amount of RF energy passing therethrough.

From the foregoing, it will be seen that this invention is one well adapted to attain all of the ends and objects herein set forth, together with other advantages which are obvious and which are inherent to it.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

Having thus described our invention, we claim:

1. An electrostatic shield for use with shortwave diathermy apparatus having a diathermy applicator head, said shield adapted to be located between the diathermy applicator head having current carrying coils therein and the body of the patient being treated, said shield comprising:
   means for attenuating electrostatic energy emanating from said head reaching said patient, said attenuating means comprising electrically conductive strips located between said current carrying coils in said head and said patient; and
   means for grounding and attenuating means.

2. The combination as in claim 1 wherein said strips define a plane which is substantially parallel to the plane of said coils.

3. The combination as in claim 1 including means for mounting said shield on said applicator head.

4. The combination as in claim 3 wherein said strips define a plane which is substantially parallel to the plane of said coils.

5. The combination as in claim 1 including loop means for reducing electrostatic fringing, said loop means being electrically connected to said attenuating means.

6. The combination as in claim 5 wherein said strips define a plane which is substantially parallel to the plane of said coils and the plane of said loop.

7. The combination as in claim 6 wherein said loop is substantially the size of said applicator head.

8. The combination as in claim 6 wherein said strips extend generally radially outwardly from the center of the area defined by said loop, said strips being electrically connected to said loop.

9. The combination as in claim 8 wherein the center of the area defined by said loop has at least a portion thereof which is not occupied by said strips.

10. The combination as in claim 8 wherein said strips are coplanar with said loop.

11. The combination as in claim 10 wherein the center of the area defined by said loop has at least a portion thereof which is not occupied by said strips.

12. The combination as in claim 11 including means for mounting said shield on said applicator head.

13. A variable electrostatic shield for use with shortwave diathermy apparatus, said shield adapted to be located between a diathermy applicator head having current carrying coils therein and the body of the patient being treated, said shield comprising:
   first and second shield surfaces, each of said surfaces comprising means for attenuating electrostatic energy reaching said patient and loop means for grounding said attenuating means, said attenuating means comprising a plurality of electrically conductive strips located between said current carrying coils and said patient; and
   means for mounting said first shield surface for rotation with respect to said second shield surface.

14. The combination as in claim 13 wherein said strips are oriented substantially perpendicular to said loop means.

15. The combination as in claim 13 wherein said first and second shield surfaces have a central area which is not occupied generally radially outwardly from said area.

16. A method for using a radio frequency diathermy apparatus with at least one applicator head in therapeutic heat treatment of internal body tissues and for simultaneously limiting the surface skin heating associated with said treatment, said method comprising the steps of:
   generating radio frequency electric currents in said diathermy apparatus to thereby produce electrostatic and electromagnetic energy in said treatment head;

directing said electrostatic and electromagnetic energy toward the body tissue via said diathermy applicator head;

attenuating at least a portion of said electrostatic energy reaching the exterior skin surface to thereby limit said exterior heating effect; and transcutaneously heating the body tissue to be treated by said electromagnet energy.

17. The method as in claim 16, wherein the attenuating step includes locating an electrostatic shield means between said diathermy applicator head and the exterior skin surface.

18. The method as in claim 16, wherein the attenuating step includes mounting the electrostatic shield means on said diathermy applicator head.

19. The method as in claim 17, wherein the step of attenuating said electrostatic energy includes the further step of varying the effect of the electrostatic shield means on the electrostatic energy thereby controlling the amount of electrostatic energy passing through said electrostatic shield means.

20. The method as in claim 18, wherein the step of attenuating said electrostatic energy includes the further step of varying the effect of the electrostatic shield means on the electrostatic energy thereby controlling the amount of electrostatic energy passing through said electrostatic shield means.

* * * * *

UNITED STATES PATENT AND TRADEMARK OFFICE
CERTIFICATE OF CORRECTION

PATENT NO. : 4,068,292
DATED : January 10, 1978
INVENTOR(S) : Fred M. Berry & James N. Shirley It is certified that error appears in the above-identified patent and that said Letters Patent are hereby corrected as shown below:

Please correct the address of the assignee (International Medical Electronics, Ltd.) to read:

Kansas City, Missouri instead of Kansas City, Kansas

Signed and Sealed this

Sixth Day of June 1978

[SEAL]

Attest:

RUTH C. MASON
*Attesting Officer*

DONALD W. BANNER
*Commissioner of Patents and Trademarks*

UNITED STATES PATENT AND TRADEMARK OFFICE
CERTIFICATE OF CORRECTION

PATENT NO. : 4,068,292
DATED : January 10, 1978
INVENTOR(S) : Fred M. Berry and James N. Shirley It is certified that error appears in the above-identified patent and that said Letters Patent are hereby corrected as shown below:

Column 6, line 4, should read -- means for grounding said attenuating means.

Signed and Sealed this

Seventh Day of August 1979

[SEAL]

Attest:

*Attesting Officer*

LUTRELLE F. PARKER
*Acting Commissioner of Patents and Trademarks*